US00PP33182P3

(12) United States Plant Patent
Klettke

(10) Patent No.: US PP33,182 P3
(45) Date of Patent: Jun. 22, 2021

(54) HEMP PLANT NAMED 'PAINTED LADY'

(50) Latin Name: ***Cannabis* hybrid**
Varietal Denomination: Painted Lady

(71) Applicant: Jeremy Klettke, Bend, OR (US)

(72) Inventor: Jeremy Klettke, Bend, OR (US)

( * ) Notice: Subject to any disclaimer, the term of this patent is extended or adjusted under 35 U.S.C. 154(b) by 0 days.

(21) Appl. No.: 16/602,561

(22) Filed: Oct. 30, 2019

(65) Prior Publication Data

US 2021/0136973 P1 May 6, 2021

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258, 263.1
CPC ... A01H 5/02; A01H 5/12; A01H 5/00; A01H 6/12; A01H 6/28; A61K 36/185
See application file for complete search history.

(56) References Cited

PUBLICATIONS

Allbud Oracle Strain 2020, retrieved from the Internet at May 4, 2020, retrieved from the Internet at https://www.allbud.com/marijuana-strains/hybrid/oracle, 4 pp. (Year: 2020).*
Oklahoma Department of Agriculture Food and Forestry 2019, retrieved on Apr. 30, 2020, retrieved from the Internet at http://ag.ok.gov/cps/CertifiedHempSeedList.pdf, 7 pp. (Year: 2019).*
Trademark Electronic Search System (TESS) for Painted Lady, retrieved on Apr. 30, 2020, retrieved from the Internet at http://tmsearch.uspto.gov/bin/showfield?f=doc&state=4803:hovmx5.2.1, 2 pp. (Year: 2020).*
Trademark Manual of Examining Procedure (Oct. 2018), retrieved on Apr. 30, 2020, retrieved from the Internet at https://tmep.uspto.gov/RDMS/TMEP/current#/current/TMEP-1200d1e2820.html, 2 pp. (Year: 2018).*
Upov International Union for the Protection of New Varieties of Plants UPOV/INF/12/5, 2015 retrieved on Apr. 30, 2020, retrieved from the Internet at https://www.upov.int/edocs/infdocs/en/upov_inf_12.pdf, pp. 1, 3-8. (Year: 2015).*
Proven Winners, (2015). "Double Play Painted Lady Pamphlet," 2 pages.
Proven Winners, (2015). "Double Play Painted Lady Product Tag" 1 page.
Davis Herb Farms, "Michigan Cannabis Expo Ad," made available on Oct. 4, 2019, 1 page.
Davis Herb Farms, "Ohio Hemp Summit Brochure Ad," made available on Aug. 30, 2019, 1 page.
Davis Herb Farms, (2019). "CBD Rich Industrial Hemp Seed Ad," Grow Magazine Quarter PG, made available on Oct. 16, 2019, 1 page.

* cited by examiner

*Primary Examiner* — June Hwu
(74) *Attorney, Agent, or Firm* — Morrison & Foerster LLP

(57) ABSTRACT

A new and distinct cultivar of hemp (*Cannabis*) named 'Painted Lady' is disclosed, characterized by a 30:1 median ratio of Cannabidiol (CBD) to Tetrahydracannabinol (THC) at time of harvest, green hollow stem with red and purple hues, purple pistillate inflorescence with short white stigma, high yield potential, high frost tolerance, pest, disease, and mildew resistance, and low hermaphroditic potential in the female plant.

5 Drawing Sheets

FIELD OF THE INVENTION

Botanical classification: *Cannabis* hybrid.
Variety denomination: 'Painted Lady'.

BACKGROUND OF THE INVENTION

The present invention comprises a new and distinct hemp cultivar, hereinafter referred to by the cultivar name, 'Painted Lady'. It is noted that "hemp" is a term used to describe varieties of *Cannabis* that contain 0.3% or less Tetrahydrocannabinol (THC) content by dry weight.

The inventor, Jeremy Klettke, discovered the new cultivar as a result of crossing two stabilized open source (unpatented) parents, hybridized from the species *Cannabis sativa* L. and *Cannabis indica*. More specifically, 'Painted Lady' was discovered through a series of outdoor field trials carried out in 2016, 2017, and 2018, combined with a number of parallel indoor pollination projects at Mr.

Klettke's breeding facility in LaPine, Oreg. 'Painted Lady' was the result of working with more than 12,000 individual variations of this hybrid.

Further developed in a closed environment breeding program, carried out indoors, 'Painted Lady' is characterized as a high yielding cultivar for Cannabidiol (CBD) production containing very low quantities of THC, Cannabigerol (CBG), Resorcinol, 2-(3,7-dimethyl-2,6-octadienyl)-5-pentyl, Cannabichromenic Acid (CBC-A), 5-hydroxy-2methyl-2-(4-methylpent-3-enyl)-7-pentyl-chromene-6-carboxylic acid.

Asexual reproduction of the new cultivar has been done by stem propagation or cutting performed at Mr. Klettke's breeding facility in LaPine, Oreg. The unique features of this cultivar are stable and reproduced true to type through successive generations. This is a cultivar bred for plant resin production, containing quantifiable amounts of cannabinoids and terpenes with little to no psychoactivity.

SUMMARY OF THE INVENTION

In the following description, color references are made to The Royal Horticultural Society Colour Chart (R.H.S. Colour Chart), 6th edition, 2015, except where general terms of ordinary dictionary significance are used.

The term "cultivar" is used herein interchangeably with "variety" "strain," and/or "clone."

The cultivar 'Painted Lady' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Painted Lady'. These characteristics in combination distinguish 'Painted Lady' as a new and distinct hemp cultivar:

1. This plant is stable and quick growing.
2. This plant displays strong pest and disease resistance.
3. This plant is highly frost resistant, and resistant to powdery mildew (*Podosphaera xanthii*), grey mold or botrytis (*Botrytis cinerea*), and white mold (*Sclerotinia sclerotiorum*).
4. This plant contains high quantities of the compound CBD and low quantities of THC or any other intoxicating compound, with a median CBD to THC ratio of 30:1. The range percentage by weight of the CBD content is 7-9%, and the range percentage by weight of the THC content is 0.2-0.3%.
5. This plant contains significantly higher quantities of the terpenes beta-Myrcene, beta-Caryophyllene, Ocimene Isomer II, alpha-Pinene, beta-Pinene, alpha-Humulene, alpha-Bisabolol, Limonene, and endo-fenchyl alcohol than either of its parents. As determined by liquid chromatography, the range percentages by weight of the terpenes are 0.75-3.5%.
6. This plant has low hermaphroditic potential in the female plant.
7. This plant displays strong tendencies to branch without traditional horticultural manipulation techniques.
8. This plant displays a unique non-alternating branching pattern in cloned plant examples.

BRIEF DESCRIPTION OF THE DRAWINGS

Colors in the photographs may appear different from the color values that appear in the detailed botanical description which more accurately describe the new cultivar.

The photographs were taken using conventional techniques and, although colors may appear different from actual colors due to light reflectance, it is as accurate as possible by conventional photographic techniques.

DETAILED DESCRIPTION OF THE PREFERRED EMBODIMENTS

Figure 1:
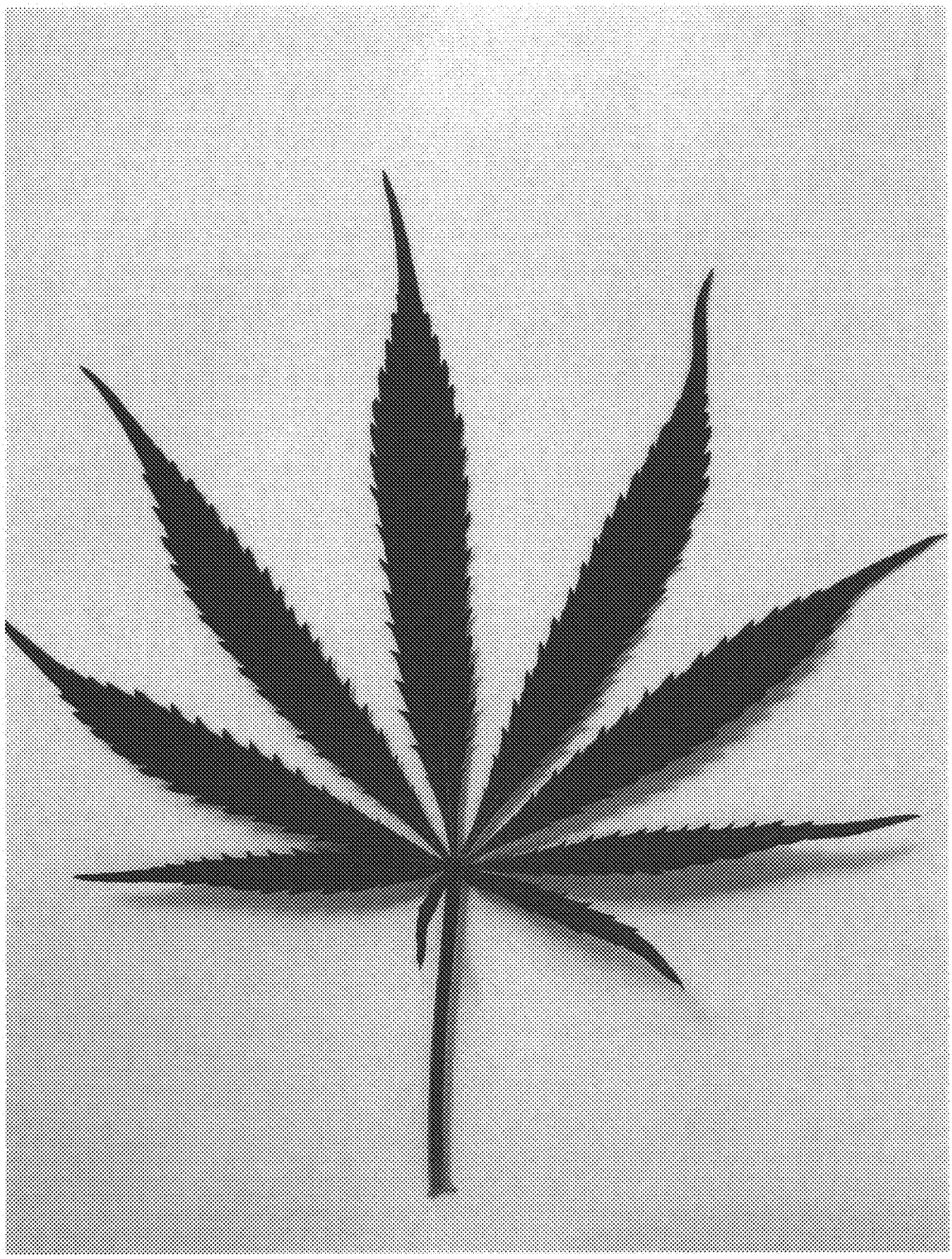
FIG. 1 is a top view of a plant of 'Painted Lady', showing a developed water leaf.
Figure 2:
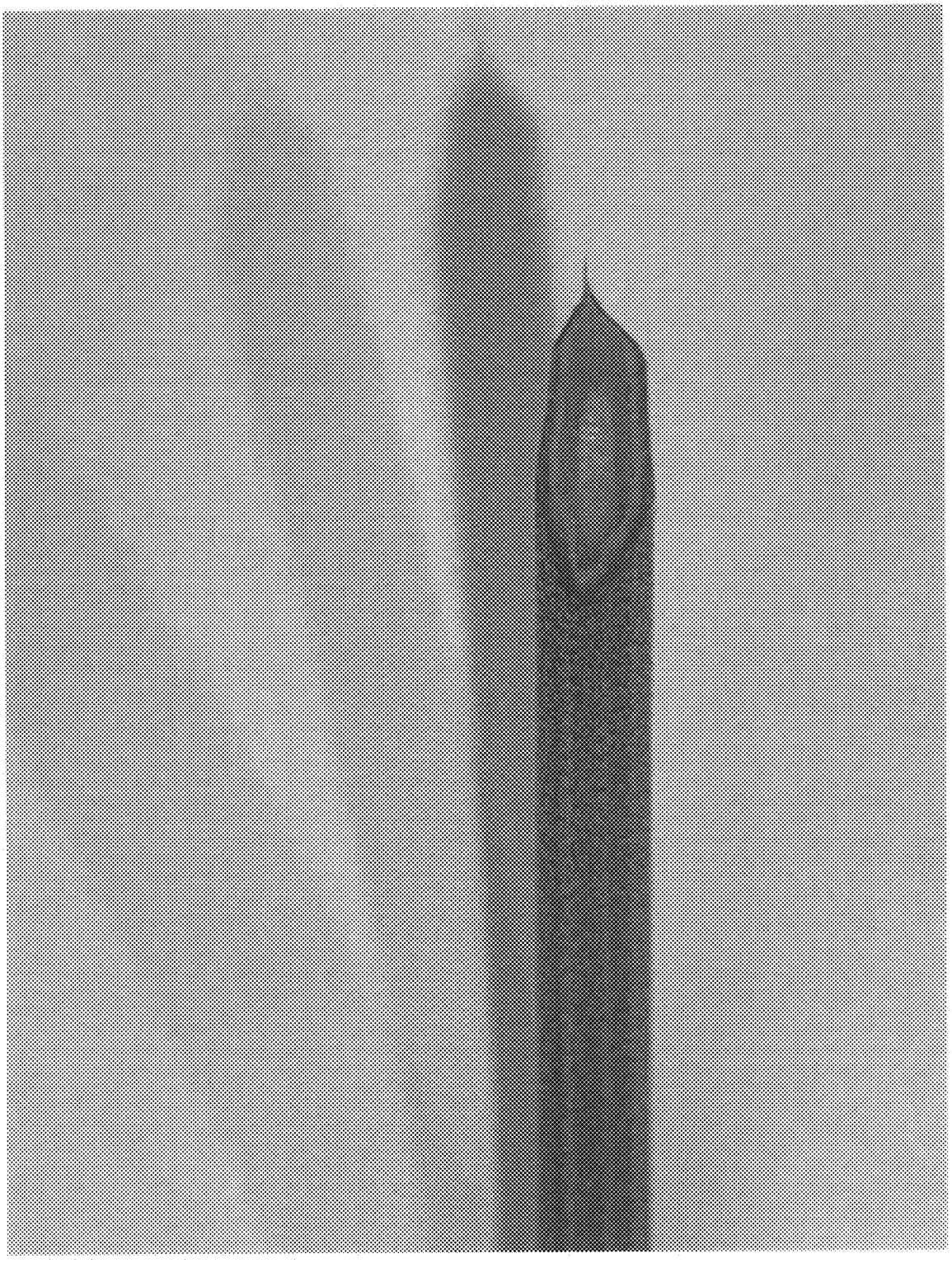
FIG. 2 is a side view of a plant of 'Painted Lady', showing a cross-section of a cut stem.
Figure 3:
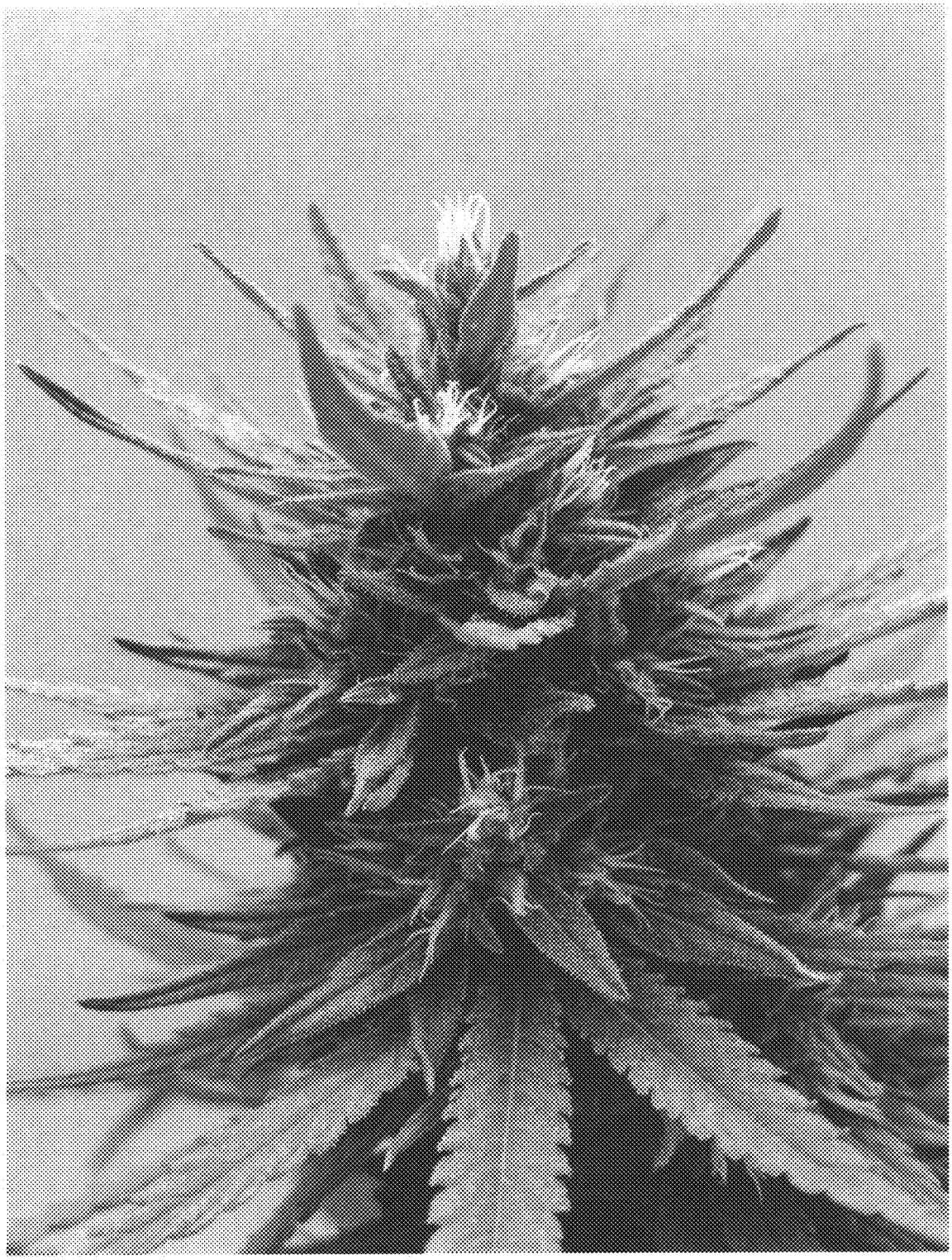
FIG. 3 is a side view of a plant of 'Painted Lady', showing an immature, partially developed flower.
Figure 4:
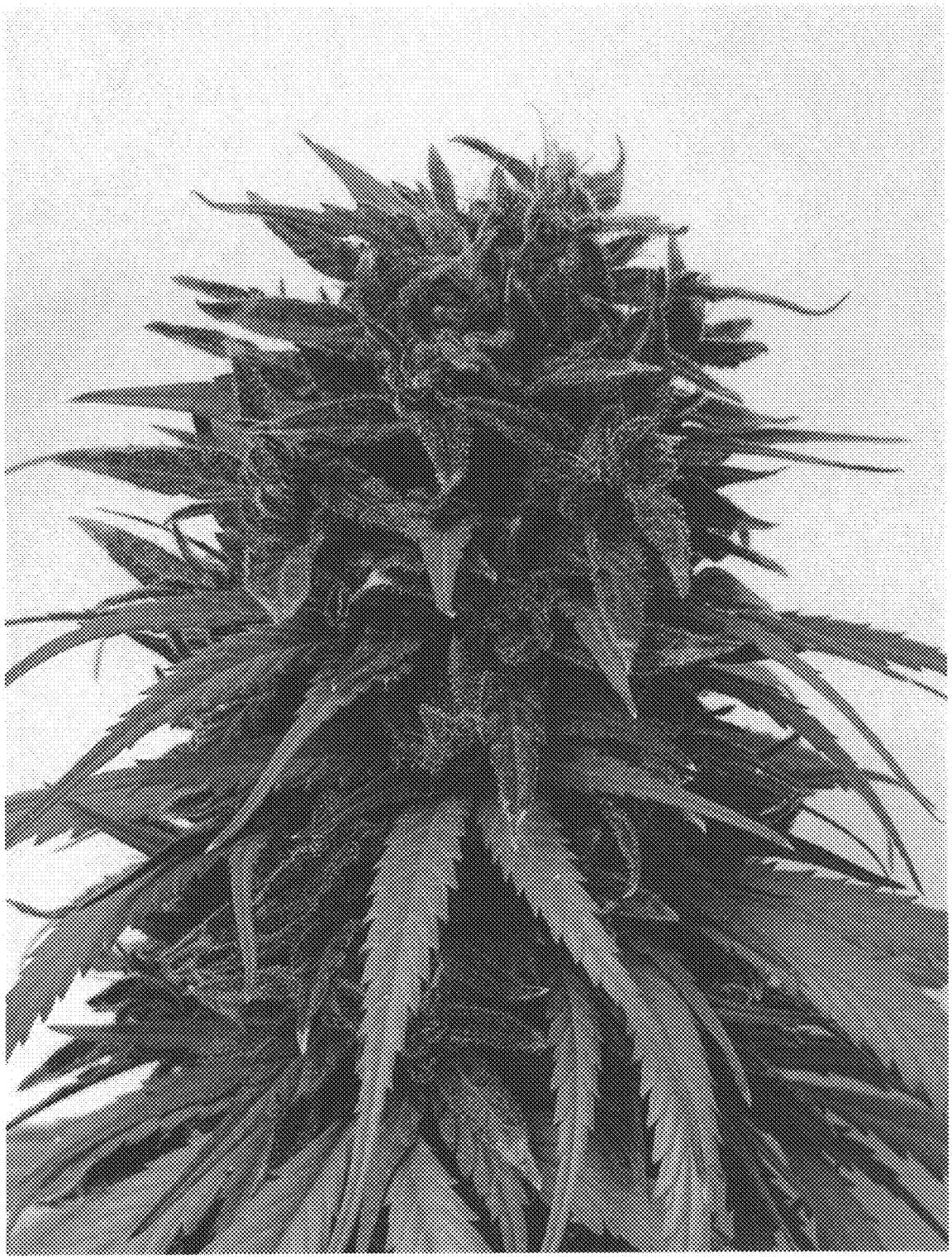
FIG. 4 is a side view of a plant of 'Painted Lady', showing a mature, developed flower.
Figure 5:
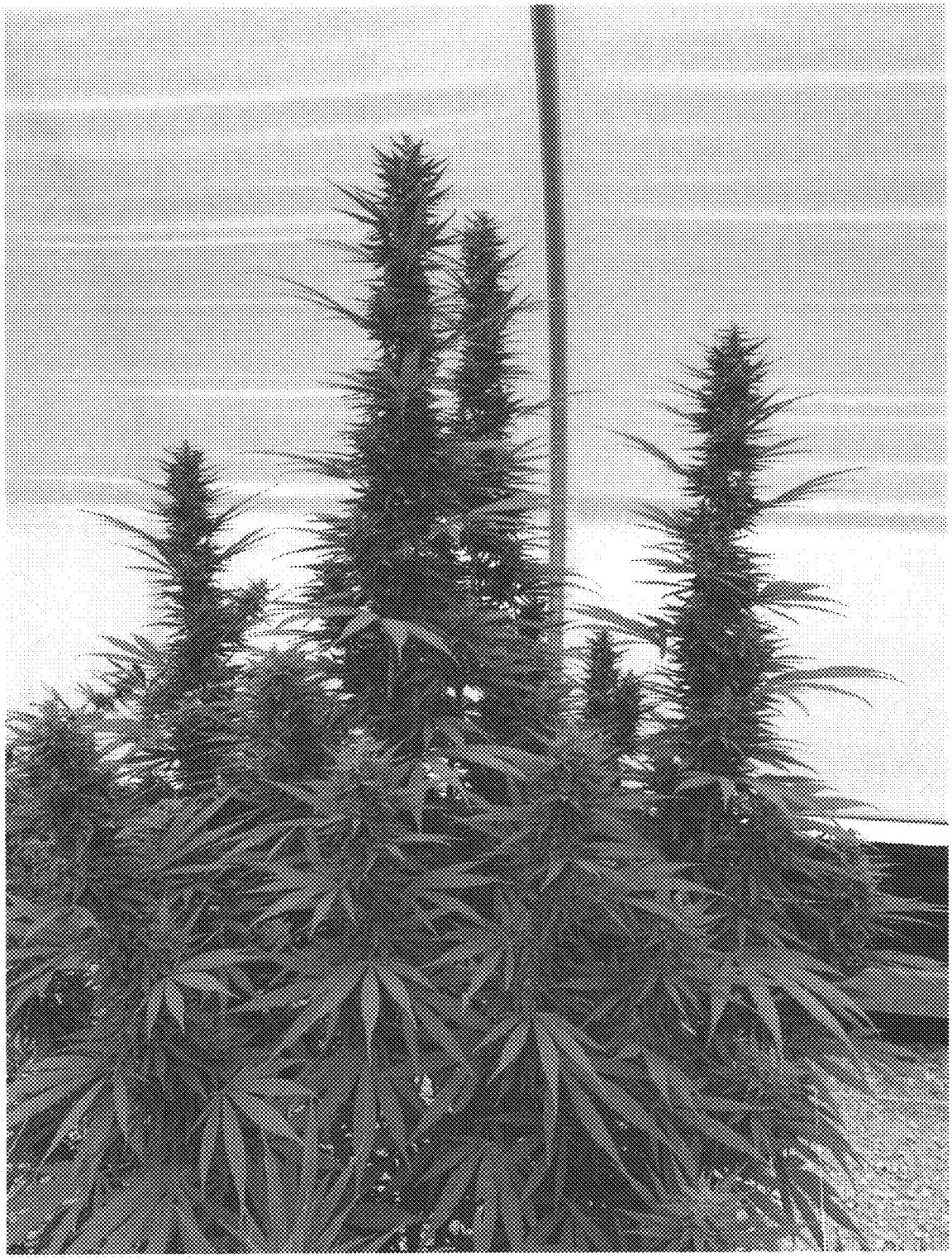
FIG. 5 is a side view of a plant of 'Painted Lady', showing a whole, mature plant.

This invention relates to a new hemp plant hybrid of *Cannabis sativa* L. and *Cannabis indica* named 'Painted Lady'. 'Painted Lady' is a plant bred for indoor and outdoor production of plant resin containing high quantities of the compound CBD and low quantities of THC or any other intoxicating compound. The present plant was developed over 3.5 years at Mr. Klettke's breeding facility in LaPine, Oreg., using parents selected from open source unstabilized dioecious seed and propagated cuttings. The plant can be grown in most climates through a normal summer growing season from 38-48 degrees of latitude either North or South of the equator. Although this plant is primarily dependent on the photoperiod for flowering, it can be grown throughout a large part of the year in latitudes within 10 degrees of the equator.

Parentage:

*Seed.*—Unnamed *Cannabis* hybrid 'Oracle' x 'Otto II' #103.

*Pollen.*—Unnamed *Cannabis* hybrid 'Oracle' x 'Otto II' #259.

The parent plants of 'Painted Lady' consist of a mother and a father developed from an elite, open source clone named 'Oracle' crossed with an unstabilized open source male named 'Otto II' which was selected from seed. 'Oracle' is a stable resin producing female with a CBD to THC ratio of 20:1 and has been available in limited circles of *Cannabis* cultivators and breeders. 'Oracle' is a short growing bushy plant with 1-1.5 inch internodal spacing with moderately broad leaf structure. 'Otto II' was developed and released in seed form as a CBD producing hemp cultivar for outdoor production. 'Otto II' contains small but measurable amounts of terpenes and very little THC with ratios of CBD to THC ranging from 15:1 through 25:1.

The claimed plant 'Painted Lady' has been stabilized and has a median CBD to THC ratio of 30:1. 'Painted Lady' also contains significantly higher quantities of terpenes than either of its parents and has been bred to avoid hermaphroditic potential in the female plant.

TABLE I

| | |
|---|---|
| LATIN NAME OF THE FAMILY, GENUS AND SPECIES | *Cannabis* hybrid |
| VARIETY DENOMINATION | 'Painted Lady' |
| MARKET CLASS | Hemp |
| PROPAGATION | Typically propagated asexually via stem cuttings and F1 rootstock. Cloning is performed in a propagation chamber with low par reduced spectrum lighting. The propagation chamber has reduced environmental variablity to maintain a relative humidity at or about 75% and a constant temperature of 72 degrees Fahrenheit. |
| PLANT DESCRIPTION | Bush-like structure. This branching of this structure is further broadened by removing the terminal flower. The natural height of the plant at annual harvest (maturity) is 4-5 feet, and the width is 5.5-7 feet. The plant is primarily self supporting through its life cycle. |
| STEM DESCRIPTION | Hollow ribbed stem with some red and purple striping on the more mature woody parts. Stem thickness is medium, stem depth of ribbing is medium, and stem pith in cross-section is medium. Stems are strong with a tendency to bend rather than snap. Texture is coarse due to sessile glands covering the surface. Color is wintergreen (RHS 128A) changing to emerald green (RHS N134C) at maturity. |

TABLE I-continued

| | |
|---|---|
| BUD DESCRIPTION | Early flower development and resin production in flowering, comparatively short broad stigmas that are consistently white (RHS N155C) in color. Finished buds or pistillate inflorescences range in size from 16-24 inches in length on the primary branches, with broken internodal buds continuing down the branches for 3 feet toward the base of the plant with increased sparsity. Finished buds range in diameter from 2-3 inches at the top of the branch down to 0.5 inches towards the base of the plant. Finished buds range in color from light green (RHS 140C) to purple (RHS N74A). |
| LEAF DESCRIPTION | Each leaf is compound and contains either 7 or 9 leaflets with uniform and mild serration. The leaflets are narrow with moderate separation at the base. The average leaf length is 3 inches, the central leaflet average length is 3.5-4 inches, and the central leaflet average width is ⅝ of an inch The leaf surface texture is rough on the top due to stiff hairs and both sides are covered with sessile glands. The leaf fragrance is lavender with fruity mango notes. The upper leaf surface color is strong yellowish green (RHS 134B) and the lower leaf surface color is strong yellow green (RHS 142A). The venation pattern is primarily palmate, serrated leaflets with no double serration only a single vein to each serrated tip. The leaf has unique exaggerated serrations.<br>The petiole has an average length of 2 inches and an average diameter of 4 mm. The petiole trichome type is a sessile gland with limited to no capitate head. The petiole intensity of anthocyanin is weak, and the petiole color is brilliant yellowish green (RHS 134C). The stipule is 1/16-⅛ of an inch in size, and narrow and needle-like in shape. The stipule contains no visible trichomes. The stipule color is brilliant yellow green (RHS 142B). |
| FLOWER DESCRIPTION | The primary flowers when finished are large at 2.5-3 inches in diameter and 16-24 inches long on average, very dense or tight in structure, covered densely in trichomes. The flowers have a high calyx to leaf ratio which provides stronger cannabinoid production. The finished flower is highly resinous and aromatic. The appearance of the dried flower is sparkling with trichomes. The leafy parts of the flower (primarily sugar leaves) retain green as a base color mixed with red, purple, and blue hues. The pistillate inflorescence is moderate purplish red (RHS 186B) and the stigma remains white until maturity. The immature stigma color is light yellow green (RHS 144D), and the mature stigma color is dark greenish yellow (RHS 152C). The average length of the stigma is 4 mm. The flowering season is May through October. The average bract size is 1-1.5 cm, and the bract quantity per flower is several dozen (the flower size can vary significantly depending upon the flower location on the plant as well as the overall size of the plant). The bract shape is oval, and the bract trichome type is sessile. The bract color is strong yellowish green (RHS 141C). The average bracteole size is 2-3 mm, and the bracteole quantity per flower is 4-6. The bracteole has a sessile trichome type. The bracteole shape is arrow-like, and the bracteole color is brilliant green (RHS 128A). The average sugar leaf size is 10 cm. The sugar leaf has both glandular and non-glandular trichome types. The sugar leaf color is strong yellowish green (RHS 141C). |

TABLE I-continued

| | |
|---|---|
| FRUIT DESCRIPTION | The fruit type is pistillate inflorescence. The fruit shape is a tall and fat pinecone shape. The average size of the fruit is 4 inches in diameter and 7 inches in length. The fruit color is deep purplish red (RHS 187D). |
| ROOT DESCRIPTION | Short taproot from seed that is generally not deeper than 30 cm at maturity. There are dense subsurface lateral roots spreading out to 70 cm from the base of the plant. |
| SEED DESCRIPTION | The seeds are 2.5-3 mm long with a slightly oval shape that has a depression at one end and a rounded point at the opposite end. The seeds are dark purple to black in color. With veins throughout the leaf surface when closely observed. The seed color of testa is greyish yellow green (RHS 198A), and seed marbling is medium. The average weight per 1000 seeds is low (less than 10 grams). |
| FRAGRANCE/TASTE | Sharp astringent tropical fruit odor with notes of blueberries and anise in the ripe flower/bud. The stem also produces a sour aroma with notes of blueberry when rubbed. |
| GROWTH HABIT | Annual, dioecious, erect herb. Unique internodal spacing consisting of two nodes 1 inch apart separated by a 2.5-3 inch gap then followed again by 2 nodes separated by 1 inch. |
| DISEASE RESISTANCE | Naturally pest and disease resistant. Bred from pest, pathogen, and virus free mother stock to reduce the potential for any predisposition for a virus or pathogen to influence the genetic material.<br>The plant has shown resistance to the pests fall armyworm (*Spodoptera ornithogalh*), two spotted spider mite (*Tetranychus urticae*), and broad mite (*Polyphagotarsonemus latus*). The plant is resistant to most common molds, including Botrytis cinerea, and powdery mildews, such as *Podosphaera xanthii*. In addition, the plant has shown some resistance to Hyphomycetes such as *Fusarium* spp. |
| PRODUCTIVITY | The plant is grown annually in a moderate climate with a growing season of 5 to 6 months. Over an average growing summer, the plant will yield 1.5-2.5 lbs. of dried plant material. Average time from planting to harvest is 4.5-5.5 months. The shipping quality is high. The market use is for oil production and smokable flower production. The storage life is 3-6 months depending on storage climate. |
| TEMPERATURE TOLERANCE | Frost resistance down to 28° Fahrenheit as a young sapling. Frost resistance down to 22° Fahrenheit as a mature flowering plant |
| GROWTH CYCLE | Outdoor: Annual from March to October. Indoor: Photoperiod dependent vegetative cycle with an approximate 50 day flowering cycle. |

COMPARISON TO RELATED KNOWN CULTIVAR

'Painted Lady' is distinguished from 'Eighty Eight' (U.S. Plant patent application Ser. No. 16/602,563) in that the plant of 'Painted Lady' is slightly taller in height than the plant of 'Eighty Eight'. Further, the flowers of 'Painted Lady' have internode spacing that is more spread out, which provides the flowers with a longer appearance than the flowers of 'Eighty Eight'. In addition, the overall color palette of 'Painted Lady' is lighter than the overall color palette of 'Eighty Eight'.

What is claimed is:

1. A new and distinct cultivar of hemp plant named 'Painted Lady' as illustrated and described.

* * * * *